(12) United States Patent
El-Rashidy

(10) Patent No.: US 8,889,125 B2
(45) Date of Patent: Nov. 18, 2014

(54) TREATMENT OF HUNTINGTON'S DISEASE

(71) Applicant: Genix Therapeutics Group, LLC, Wheeling, IL (US)

(72) Inventor: Ragab El-Rashidy, Deerfield, IL (US)

(73) Assignee: Genix Therapeutics Group, LLC, Skokie, IL (US)

( * ) Notice: Subject to any disclaimer, the term of this patent is extended or adjusted under 35 U.S.C. 154(b) by 0 days.

(21) Appl. No.: 13/838,631

(22) Filed: Mar. 15, 2013

(65) Prior Publication Data
US 2014/0271592 A1 Sep. 18, 2014

(51) Int. Cl.
*A61K 38/43* (2006.01)
*A61K 31/714* (2006.01)
*A61K 31/455* (2006.01)
*A61K 31/7076* (2006.01)
*A61K 31/51* (2006.01)

(52) U.S. Cl.
CPC ............. *A61K 31/714* (2013.01); *A61K 31/455* (2013.01); *A61K 31/7076* (2013.01); *A61K 31/51* (2013.01)
USPC .................... 424/94.1; 536/26.13; 536/26.21; 536/26.24; 536/26.4

(58) Field of Classification Search
None
See application file for complete search history.

(56) References Cited

U.S. PATENT DOCUMENTS

2006/0257502 A1* 11/2006 Liu ............................... 424/682

OTHER PUBLICATIONS

Browne, S.E., Annals of the New York Academy of Sciences, 2008, vol. 1147, p. 358-382.*
Mochel et al., The Journal of Biological Chemistry, 2012, vol. 287, No. 2. p. 1361-1370.*
SEDICO "Adeno-Sed B Forte" drug information, 2004, 1 page.*

* cited by examiner

*Primary Examiner* — Kade Ariani
(74) *Attorney, Agent, or Firm* — Olson & Cepurtis, Ltd.

(57) ABSTRACT

The present invention relates to a method of treatment and/or ameliorating the symptoms of Huntington's disease comprising the step of administering an effective amount of adenosine triphosphate, co-carboxylase, nicotinamide, and cyanocobalamin in a physiologically acceptable carrier to an individual in need thereof. Preferably, the administration is via intramuscular injection.

3 Claims, No Drawings

TREATMENT OF HUNTINGTON'S DISEASE

FIELD OF THE INVENTION

The present invention relates to treatment and/or amelioration of symptoms due to Huntington's disease and other related diseases due to polyglutamine accumulation and toxicity.

BACKGROUND OF THE INVENTION

Huntington's disease is an inherited, severely disabling, neurodegenerative disorder without curative or preventative treatment. It is caused by a genetic defect on chromosome 4. The defect causes a portion of the DNA, called a CAG repeat, to occur many more times than it is supposed to. Normally this section of DNA is repeated 10 to 28 times but in person's with Huntington's disease, it is repeated 36 to 120 times. As the gene is passed down through families the number of repeats tends to get larger. The larger the number of repeats, the greater the chance of developing symptoms at an earlier age.

Huntington's disease is a member of a group of diseases occurring due to polyglutamine accumulation and toxicity. It has a broad impact on a person's functional abilities and often results in movement, cognitive, and psychiatric disorders. Most people with Huntington's disease develop signs and symptoms in their mid-thirties to forties, but the onset could occur earlier or later in life. Symptoms include behavioral changes such as: hallucinations, irritability, moodiness, and restlessness; physical changes such as: facial movements, head turning to shift eye position, quick, sudden jerky movements of the arms, legs, or face, and slow uncontrolled movements; and cognitive changes such as: dementia, disorientation, loss of judgment, loss of memory, speech changes, and personality changes. Huntington's disease is ultimately fatal.

Several observations have led to the hypothesis that mitochondrial dysfunction has a role in polyglutamine diseases, and in Huntington's disease in particular. There is evidence which points to abnormal energy metabolism, elevated lactate levels, and impaired mitochondrial-complex activity. The implication of branched chain amino acids in mitochondrial intermediary metabolism, both in brain and peripheral tissues, further supports an important role for energy deficit in Huntington's disease. A reduction in adenosine triphosphate (ATP) production has been found in the brain of mice with Huntington's disease, including presymptomatic mice. In Huntington's disease patients, there is strong evidence for hypometabolism in the brain where glucose consumption is reduced, especially in the basal ganglia, even in presymptomatic mutation carriers. The underlying cause of this early energy deficit is not currently known, but impaired glycolysis, citric acid cycle, and/or oxidative phosphorylation may be involved.

SUMMARY OF THE INVENTION

The present invention provides a method for treating or ameliorating the symptoms associated with neurodegenerative diseases such as Huntington's disease. The method comprises administration of a composition comprising adenosine triphosphate (ATP), co-carboxylase, nicotinamide, and cyanocobalamin in a pharmaceutically acceptable carrier.

ATP, co-carboxylase, nicotiamide, and cyancobalamin are coadminstered, preferably by intramuscular injection, to the patient in a respective weight ratio of about 20:100:40:1 in a physiologically acceptable liquid carrier such as water, physiological saline solution, and the like.

DETAILED DESCRIPTION OF PREFERRED EMBODIMENTS

ATP is a multifunctional nucleoside triphosphate used in cells as a coenzyme. ATP transports chemical energy within cells for metabolism. It is one of the end products of cellular respiration and used by enzymes and structural proteins in many cellular processes.

Co-carboxylase, also called thiamine pyrophosphate, is a thiamine (Vitamin B1) derivative present in all living systems, in which it catalyzes several biochemical reaction. Co-carboxylase works as a coenzyme in many enzymatic reactions, such as: pyruvate dehydrogenase complex, pyruvate decarboxylase complex in ethanol fermentation, alpha-ketoglutarate dehydrogenase complex, branched-chain amino acid dehydrogenase complex, 2-hydroxyphytanoyl-CoA lyase, and transketolase.

Nicotinamide is the amide of nicotinic acid (Vitamin B3/niacin). In cells, niacin is incorporated into nicotinamide adenine dinucleotide (NAD) and nicotinamide adenine dinucleotide phosphate (NADP). NAD+ and NADP+ are coenzymes in a wide variety of enzymatic oxidation-reduction reactions.

Cyanocobalamin is the most common and widely-produced of the chemical compounds that have vitamin activity as Vitamin B12. Cyanocobalamin is usually prescribed for the following reasons: after surgical removal of part or all of the stomach or intestine to ensure there are adequate levels of Vitamin B12 in the bloodstream; to treat pernicious anemia; Vitamin B12 deficiency due to low intake from food; thyrotoxicosis; hemorrhage; malignancy; liver or kidney disease. Cyanocobalamin injections are often prescribed to gastric bypass patients having had part of their small intestine bypassed, making it difficult for B12 to be absorbed via food or vitamins. Vitamin B12 deficiency can cause severe and irreversible damage, especially to the brain and nervous system. Neurological symptoms include: sensory or motor deficiencies (absent reflexes, diminished vibration or soft touch sensation), subacute combined degeneration of spinal cord, or even symptoms of dementia and or other psychiatric symptoms such as irritability, focus/concentration problems and depressive state with suicidal tendencies.

The composition useful for practicing the present invention includes about 10 parts by weight adenosine triphosphate, about 50 parts by weight co-carboxylase, about 20 parts by weight nicotinamide, and about 0.5 parts by weight cyanocobalamin, in a pharmaceutically acceptable carrier as illustrated in Table 1, below.

TABLE 1

Therapeutic Composition

| Component | Preferred amount |
| --- | --- |
| adenosine triphosphate | 10 mg |
| co-carboxylase | 50 mg |
| nicotinamide | 20 mg |
| cyanocobalamin | 0.5 mg |

A preferred dosage form is a lyophilized composition containing about 10 mg adenosine triphosphate, about 50 mg co-carboxylase, about 20 mg nicotinamide, and about 0.5 mg cyanocobalamin reconstituted in an aqueous 0.9% saline solution.

The composition of the present invention can be administered by any means used for administration of such medications. Preferably, the composition is administered intramuscularly. More preferably, the injection is administered intramuscularly three (3) times per week, i.e. every other day.

EXAMPLE

A 66 year-old male patient presenting symptoms of Huntington's disease was treated by intramuscular injection of the therapeutic composition shown in Table 1, above. The therapeutic composition was administered intramuscularly every other day over a period of one month. After the one-month treatment, accompanied by physical therapy, the patient reported improvement in daily functioning, an improved average grip strength in the left hand (from 57 pounds to 66 pounds) while maintaining the same average grip strength (59 pounds) in the right hand.

The foregoing description is intended as illustrative and is not to be taken as limiting. Still other variants within the spirit and scope of the present invention are possible and will readily present themselves to those skilled in the art.

I claim:

1. A method for ameliorating loss of grip strength in a patient suffering from Huntington's Disease which comprises administering to the patient an effective amount of a composition comprising adenosine triphosphate, co-carboxylase, nicotinamide, and cyanocobalamin in a physiologically acceptable carrier, wherein the administration is by intramuscular injection, and wherein the effective amount administered comprises about 10 parts by weight adenosine triphosphate, about 50 parts by weight co-carboxylase, about 20 parts by weight nicotinamide, and about 0.5 parts by weight cyanocobalamin.

2. The method in accordance with claim 1 wherein the intramuscular injection is effected on alternate days.

3. The method in accordance with claim 2 wherein the effective amount administered comprises about 10 milligrams adenosine triphosphate, about 50 milligrams co-carboxylase, about 20 milligrams nicotinamide, and about 0.5 milligrams cyanocobalamin.

* * * * *